US012085507B2

(12) United States Patent
Christensen et al.

(10) Patent No.: US 12,085,507 B2
(45) Date of Patent: Sep. 10, 2024

(54) IN MASK SENSOR SYSTEM (71) Applicant: California Institute of Technology, Pasadena, CA (US)

(72) Inventors: Lance E. Christensen, Baldwin Park, CA (US); Kamjou Mansour, La Cañada Flintridge, CA (US)

(73) Assignee: California Institute of Technology, Pasadena, CA (US)

( * ) Notice: Subject to any disclaimer, the term of this patent is extended or adjusted under 35 U.S.C. 154(b) by 306 days.

(21) Appl. No.: 17/645,026

(22) Filed: Dec. 17, 2021

(65) Prior Publication Data
US 2022/0196550 A1    Jun. 23, 2022

Related U.S. Application Data

(60) Provisional application No. 63/126,989, filed on Dec. 17, 2020.

(51) Int. Cl.
*G01N 21/61* (2006.01)
*A61M 16/00* (2006.01)
*G01N 33/00* (2006.01)

(52) U.S. Cl.
CPC ......... *G01N 21/61* (2013.01); *A61M 16/0003* (2014.02); *A61M 2202/0208* (2013.01); *G01N 33/004* (2013.01); *G01N 2201/06113* (2013.01)

(58) Field of Classification Search
CPC ............... G01M 21/61; G01M 33/004; G01M 2201/06113; A61M 16/0003; A61M 2202/0208
See application file for complete search history.

(56) References Cited

U.S. PATENT DOCUMENTS

| 5,984,998 A | * | 11/1999 | Ottesen | G01N 21/39 75/375 |
| 8,399,837 B2 | * | 3/2013 | Robbins | G01N 21/05 250/343 |
| 10,786,693 B1 | * | 9/2020 | Opperman | A62B 18/02 |
| 2015/0092801 A1 | * | 4/2015 | Jensen | H01S 3/137 372/32 |
| 2017/0251952 A1 | * | 9/2017 | Harshman | A62B 9/006 |
| 2020/0072740 A1 | * | 3/2020 | Venturini | G01J 3/0208 |

OTHER PUBLICATIONS

Alonso et al., "Sensor Integrated Pilot Mask for On-Board, Real-Time, Monitoring of Pilot Breathing Gas", 48th International Conference on Environmental Systems, ICES-2018-334, Jul. 8-12, 2018, Albuquerque, New Mexico, 14 pgs.
Lou et al., "Near-infrared tunable diode laser absorption spectroscopy-based determination of carbon dioxide in human exhaled breath", Biomedical Optics Express, Nov. 1, 2019, vol. 10, No. 11, pp. 5486-5496, https://doi.org/10.1364/BOE.10.005486.

* cited by examiner

*Primary Examiner* — Kristina M Deherrera
*Assistant Examiner* — Jean F Morello (57) ABSTRACT

An in-situ sensor system that is configured to be placed inside of an oxygen mask for a pilot. The sensor system is readily placed in a position over the exhalation valve such that it can capture data from the exhaled air of the pilot. The sensor system has an optical sensor element that can capture data real time and feed the data to a control module that can subsequently be use to generate output data for the pilot and/or ground elements.

15 Claims, 8 Drawing Sheets

IN MASK SENSOR SYSTEM

CROSS-REFERENCE TO RELATED APPLICATIONS

This application claims priority to U.S. Provisional Patent Application No. 63/126,989 filed on Dec. 17, 2020, the disclosure of which is herein incorporated by reference in its entirety.

STATEMENT OF FEDERALLY SPONSORED RESEARCH

This invention was made with government support under Grant No. 80NMO0018D0004 awarded by NASA (JPL). The government has certain rights in the invention.

FIELD OF THE INVENTION

This application generally refers to in situ sensors that are configured to measure oxygen, CO2, and water vapor levels of a user. More specifically, the sensors are placed within the portion of a mask that interacts directly with a user such as a pilot.

BACKGROUND

Mask are often used by pilots in aircraft for multiple reasons. The mask can be used to house a communication device that will allow pilots to communication with other pilots or ground element. Additionally, masks can serve to provide pilots with the proper oxygen mixture in order to prevent the hypoxia that can result from various maneuvers. Hypoxia can pose a dangerous threat to pilots because it can cause physiological episodes often associated with syncope and conditions that may result in catastrophic events. Despite the long use of masks by pilots, there continue to be issues with physiological events with unknown causes.

SUMMARY OF THE INVENTION

Systems and methods in accordance with many embodiments of the invention are directed to mask systems with embedded sensors that can accurately measure, in real time, the amount of CO2 and/or water vapor that is being produced by the pilots. This measurement can serve as a benchmark in determining if a pilot is getting close having a physiological event while piloting an aircraft. Many embodiments are directed to a mask system having an air input valve and an air exit valve. The air input valve is configured to provide a breathable air mixture to the user while the exit valve is configured to allow the exhaled air to leave the mask. The mask is equipped with a sensor located over the exit valve that is configured to measure the amount of CO2 in the exhaled air.

In other embodiments, the sensor system has a main housing, wherein the main housing is configured to cooperatively engage with an exhalation valve of an oxygen mask and wherein the main housing has an opening disposed therein that corresponds with an opening in the exhalation valve of the mask. Additionally, the system has an optical transmitter housing disposed on the main housing and configured to house an optical transmitter element. The sensor additionally has an optical receiver housing disposed on the main housing and configured to house an optical receiver element, where the optical transmitter element is optically aligned with the optical receiver element such that a signal path between the optical transmitter element and the optical receiver element transects the opening in the main housing such that exhaled air from a user of the mask will pass through the signal path as it is pushed through the exhalation valve.

In still other embodiments, the optical transmitter element is a laser.

In yet other embodiments, the laser is a tunable laser.

In still yet other embodiments, the laser is tunable to a wavelength suitable for detecting CO2.

In other embodiments, the laser is tunable to a wavelength suitable for detecting H2O.

In still other embodiments, the optical transmitter housing has a power reducing aperture disposed in a front face of the housing such that the power reducing aperture effectively reduces the power output of the optical transmitter.

In yet other embodiments, the optical transmitter housing has a step-down profile producing a smaller opening at an exit end of the housing that effectively reduces the power output from the optical transmitter.

In still yet other embodiments, the laser has a maximum power output of 9.5 mW and the power reducing aperture reduces the power to less than 500 µW.

In other embodiments,

In still other embodiments, wherein the laser has a maximum power output of 9.5 mW and the smaller opening reduces the power output to less than 500 µW.

In yet other embodiments, the sensor system has a temperature sensor disposed on the main housing and configured to measure the temperature of the sensor system.

In still yet other embodiments, the sensor system has a plurality of electrical connections between the optical transmitter and the optical receiver, and an external control module, wherein the control module is configured to receive and analyze data from the sensor system.

In other embodiments, the control module is configured to analyze the relative content of CO2 and/or H2O in the exhaled air and wherein the control module further comprises one or more feedback elements to provide feedback to the user with respect to the relative content of CO2 and H2O.

In still other embodiments, the plurality of electrical connections are configured to be disconnectable from the mask through a connection port disposed on an exterior surface of the mask.

In yet other embodiments, the optical transmitter and the optical receiver are a fiber coupled laser.

Other embodiments are directed to A pilot oxygen mask system that has an in-situ sensor system, where the in-situ sensor system has a plurality of components including:
  A main housing, wherein the main housing is configured to cooperatively engage with an exhalation valve of an oxygen mask and wherein the main housing has an opening disposed therein that corresponds with an opening in the exhalation valve of the mask,
  An optical transmitter housing disposed on the main housing and configured to house an optical transmitter element,
  An optical receiver housing disposed on the main housing and configured to house an optical receiver element, and
Where the optical transmitter element is optically aligned with the optical receiver element such that a signal path between the optical transmitter element and the optical receiver element transects the opening in the main housing such that exhaled air from a user of the mask will pass through the signal path as it is pushed through the exhalation valve.

Additional embodiments and features are set forth in part in the description that follows, and in part will become apparent to those skilled in the art upon examination of the specification or may be learned by the practice of the disclosure. A further understanding of the nature and advantages of the present disclosure may be realized by reference to the remaining portions of the specification and the drawings, which forms a part of this disclosure.

BRIEF DESCRIPTION OF THE DRAWINGS

The description will be more fully understood with reference to the following figures, which are presented as exemplary embodiments of the invention and should not be construed as a complete recitation of the scope of the invention, wherein.

DETAILED DESCRIPTION OF THE INVENTION

Turning now to the drawings, systems and methods for measuring $CO_2$ and other components of a pilots exhaled air are illustrated. Many embodiments are directed to a mask that has the ability to provide an oxygen mixture to a pilot while flying. This can be either figure pilots, astronauts, etc. The oxygen mixture can be inhaled by the pilot to help maintain the appropriate blood oxygen levels. The pilot then exhales air that contains $CO_2$ from the metabolic processes within the body. The $CO_2$ is then pushed out of the mask through an exit valve. Many embodiments of the mask can be configured with an in-situ sensor system that sits within the breathing chamber of the mask in a manner that does not interfere with the user. The sensor system can be designed to measure the amount of $CO_2$ in the exhaled air from the pilot in a real time fashion as it the air is pushed out of the mask through the exit valve. Accordingly, many embodiments may position the in-situ sensor system directly over the exit valve such that the sensor is probing gas best matching the gas expelled from the lungs. The measurement of the $CO_2$ and/or water vapor can have a direct correlation on the metabolic processes within the body related to $O_2$ and $CO_2$ exchanges. This can be critical information when evaluating the possibility of a physiological event.

Sensors have been used before in conjunction with mask systems in the past to help evaluate the capnography of the pilot. Capnography is the measurement of $CO_2$ in the airway and can provide additional information related to the overall physiological state of the pilot. For example, a capnogram can help evaluate the $CO_2$ that affects the pH of the blood and indirectly affects the $O_2$ in the blood of the pilot during flight. As previously mentioned, this may have a direct correlation with potential physiological events. Accordingly, the measurement of $CO_2$ can be an important part of flight data analysis. $CO_2$ sensors are typically placed at the far end of the exhalation hose, such as a Vigilox Exhalation sensor. The Vigilox sensor can be used to measure the $CO_2$ output of the pilot as well as the surrounding cabin conditions. However, sensors external to the mask take up valuable cockpit space and suffer from measurement hysteresis and dilution which render interpretation difficult.

Figure 1A:
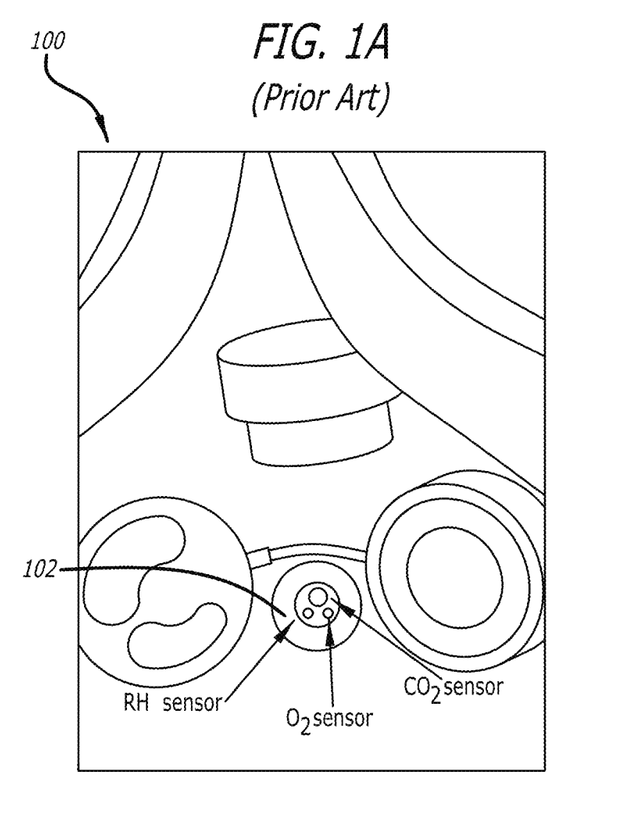
FIGS. 1A and 1B illustrate an in-situ sensor in accordance with known art.
Figure 1B:
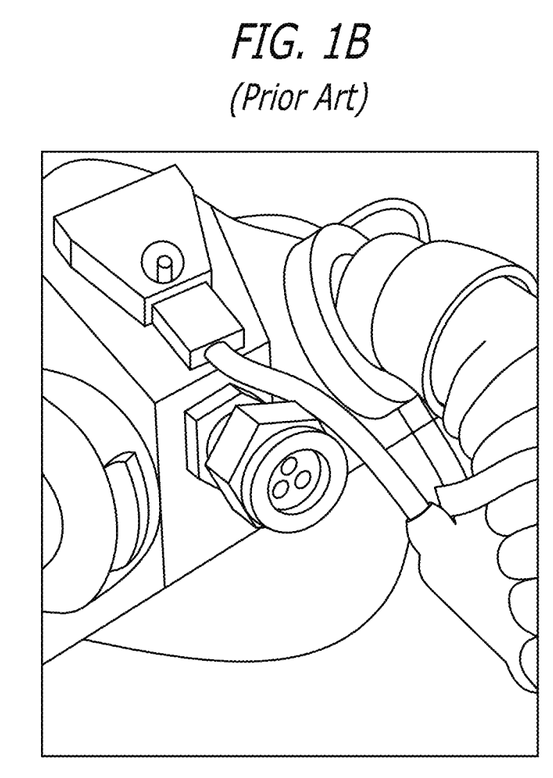

Other sensors have been placed within the mask in an attempt to overcome these inadequacies. For example, in the paper titled "Sensor Integrated Pilot Mask for On-board, Real-Time, Monitoring of Pilot Breathing Gas" by Jesus Alonso et al. (Alonso mask), a sensor is positioned in the front most portion of the mask. FIG. 1A illustrates the Alonso mask 100 with a sensor 102 positioned near the front portion of the mask 100. The Alonso mask utilizes a sensor that measures the $CO_2$ by the interaction of light with an indicator dye. The chemical reaction in the dye is what indicates the level of $CO_2$ present in the air. However, such sensors have several issues. First, the response of activated dyes to determine the level of $CO_2$ is too slow to characterize breathing cycles or mechanical flow issues and thus does gives limited insight into the dynamics of airflow to and from the pilot. Additionally, the placement of the sensor 102 in the front of the mask 100 is located in an area prone to insufficient gas exchange. As air is inhaled and exhaled by the pilot there is a pocket of gas near the front of the mask that will contain stagnant gas that is not being fully recycled out of the mask. This area can present issues in determining the most accurate level of $CO_2$ from the pilot.

Embodiments of a Mask System

Figure 2:
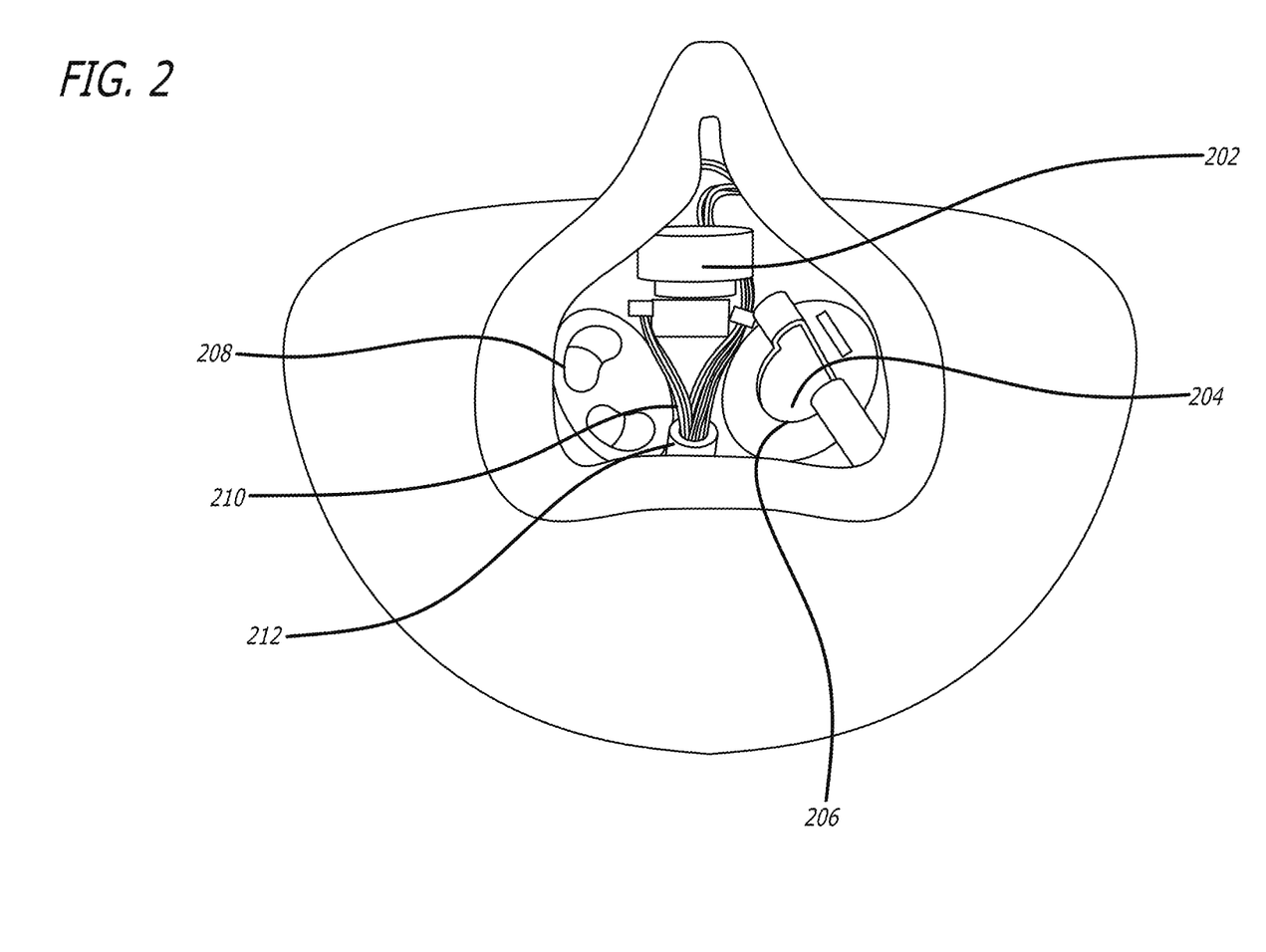
FIG. 2 illustrates an internal view of a mask configured with an air sensor in accordance with embodiments of the invention.

In contrast, numerous embodiments of the mask system described herein incorporate a sensor system strategically placed to be able to calculate a real time status of the relative $CO_2$ from the pilot. FIG. 2, for example, illustrates a mask system 200 with a voice emitter/microphone 202 and an in-situ sensor system 204. The sensor system 204 can be positioned over the exhale valve 206 such that it captures the pilot's exhaled air and presents the most accurate measure of $CO_2$ from the pilot. The position of the sensor system 204 is designed to minimize stagnant gas being measured by the sensor. Therefore, it would not be sufficient to place the sensor system 204 over the inhale valve 208 or near the front portion of the mask. Additionally, it allows for a placement within the mask that does not interfere with the pilot. Since pilots often have to wear a mask for long periods of time, it is important that the sensor does not negatively impact the pilot's comfort. As such, many embodiments of the mask system incorporate a sensor that is small enough to avoid contact with the pilot and provide accurate measurement of the $CO_2$. In accordance with many embodiments, the sensor system 204 can be connected to an external control module by way of a number of electronic connections 210 that are connected to a connection interface 212.

Figure 3A:
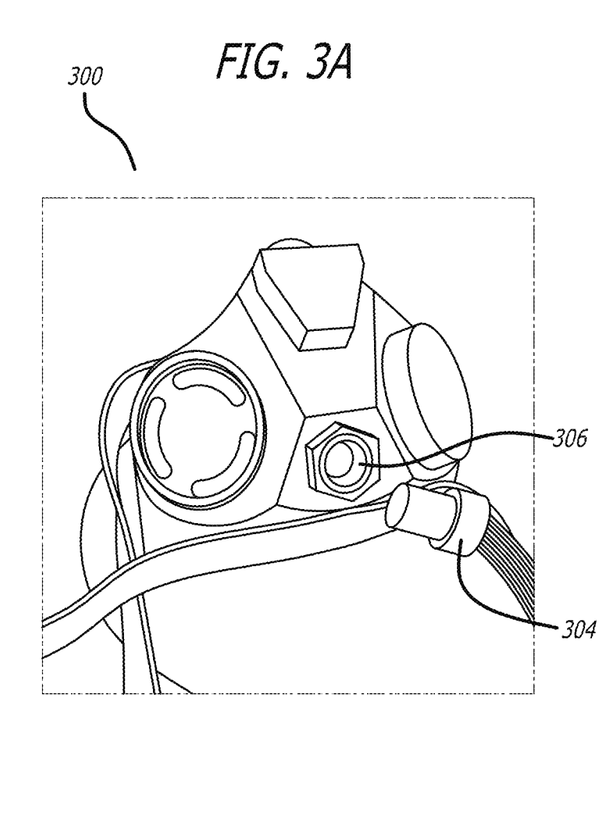
FIGS. 3A and 3B illustrate the external view of a mask with sensor connections in accordance with embodiments of the invention.
Figure 3B:
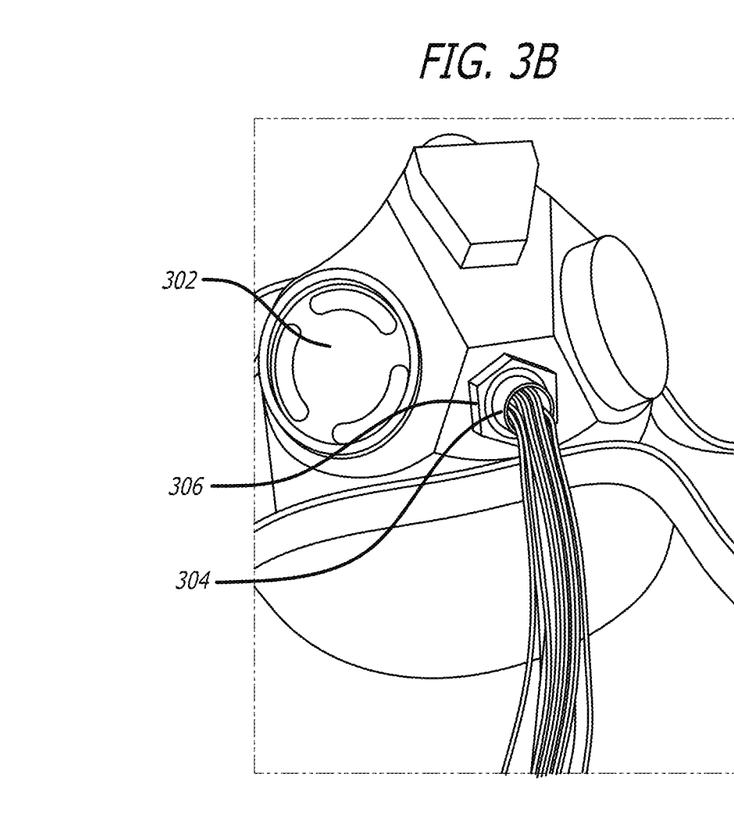

FIGS. 3A and 3B further illustrate an embodiment of a mask system 300 with an in-situ sensor system. Although not readily illustrated in FIGS. 3A and 3B, the mask system 300 is configured with a sensor system positioned over the exhale valve 302. Additionally, in various embodiments, the electronic connections 304 for the mask system 300 can be connected to a connection port 306 on the front of the mask. The connection port 306 can have an internal portion (not shown) and an external portion, where the external portion can be disconnected from the electronic connections 304 to allow for mask maintenance and or replacement. In reference to the connections 304, many embodiments may incorporate a number of connections in a wire format that transmit sensor signals from the mask to a control module (not shown). The connections 304 can take on any suitable format for transferring data and/or sensor signals to a processing unit or control module. For example, although wired connections are shown, some embodiments may implement a wireless connection.

Figure 4A:
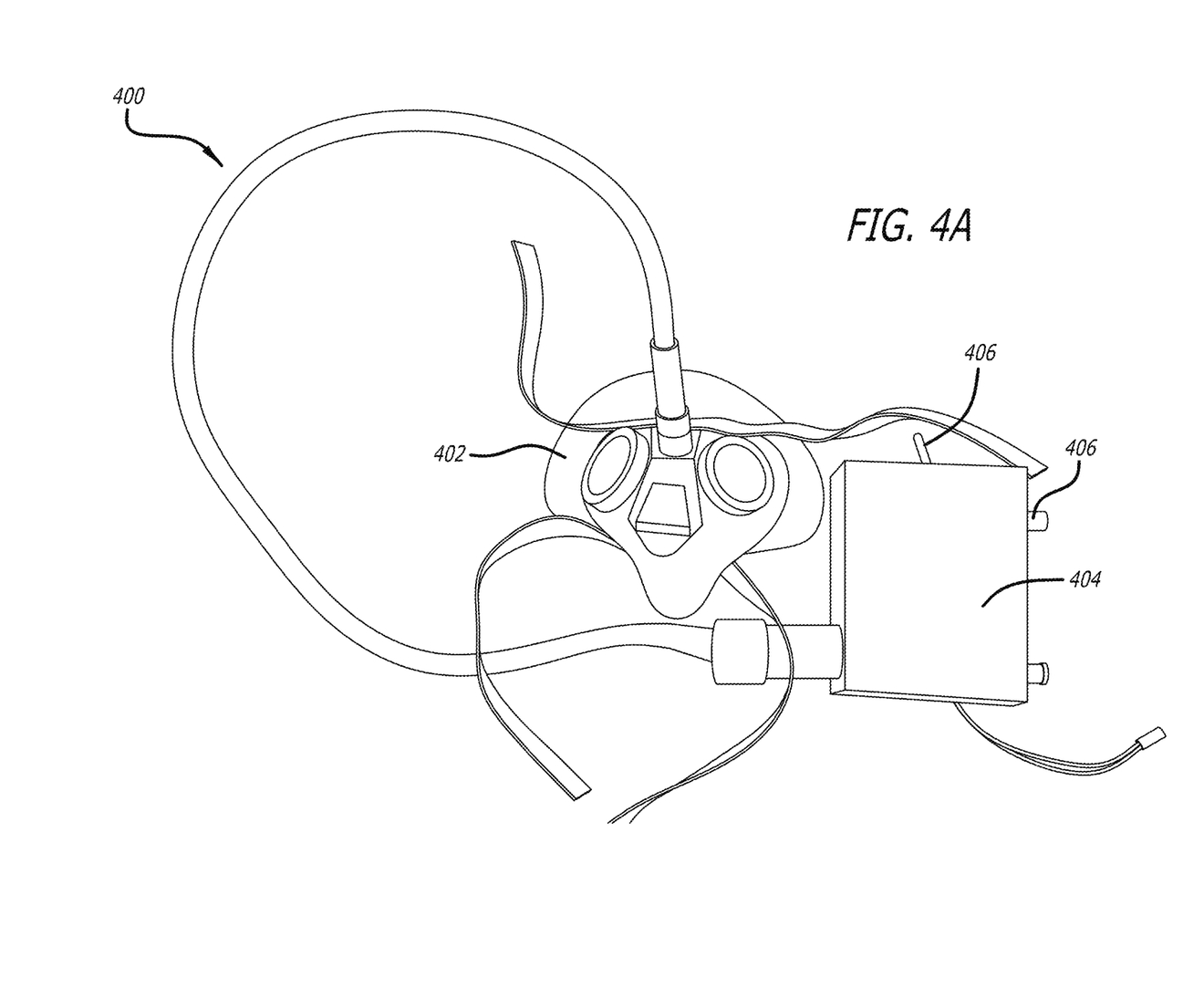
FIG. 4A illustrates a sensor system with an external control module in accordance with embodiments of the invention.

Referring now to FIG. 4A, a mask assembly 400 is illustrated. The mask assembly, can have a mask system 402 with an integrated sensor system (not shown) where the sensor system is connected to a control module 404. The control module can be configured in a number of different ways in accordance with various embodiments. Some control modules can have a separate power source while others may have a power source that is integrated. Additionally, many embodiments may incorporate a number of switches (internal and/or external) 406 that are configured to switch or activate alarms in the event of a potential physiological event is occurring or about to occur. Accordingly, the control module, according to many embodiments, is configured to receive the signals generated from the sensor system and analyze the data in various ways. For example, some control modules may be capable of generating a capnograph for future read out by an output device for real-time or future analysis. Real-time analysis in the control system consists of reducing the raw data into analyzed data that informs on pilot respiration or mechanical gas flow such as end tidal CO2 and inhaled CO2. Additionally, the control module can be configured with a particular algorithm that monitors the CO2 levels from the pilot and provides feedback and/or warnings to the pilot in real time. Such warnings can also be provided to a ground control operator to help evaluate the overall health of the pilot. This can be useful in determining the potential onset of a physiological event and prevent possible catastrophic failure. The control module can receive inputs from the pilot to mark events deemed important in order to correlate these events with data recorded by the measurement system. The control module records measurements onto a non-volatile medium such as a flash disk.

Figure 4B:
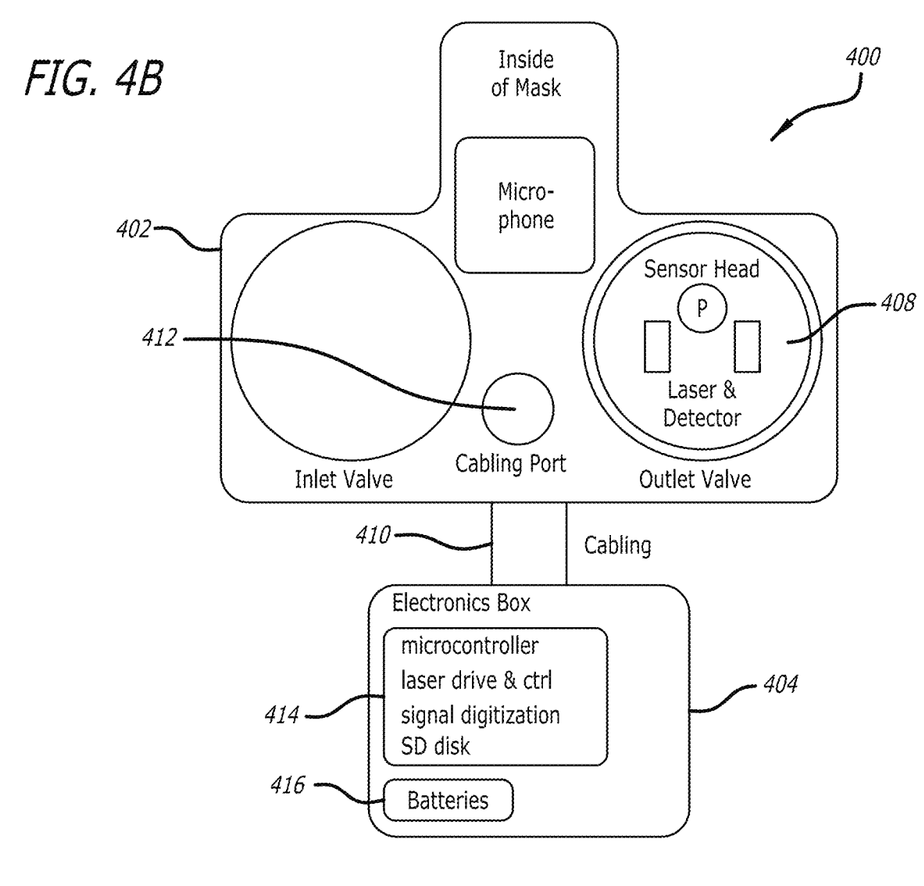
FIG. 4B illustrates an integrated sensor system with a control module in accordance with embodiments of the invention.

FIG. 4B further illustrates a schematic of a mask assembly 400 with an integrated sensor system 408. Similar to the assembly illustrated in FIG. 4A, the mask assembly 400 can be connected to a control module 404 by a cable or set of cables 410 that interface with the mask 402 through cabling port or connection point 412. In numerous embodiments the control module 404 can contain various electronic components such as a microcontroller or computer 414 that is configured to receive signals from the sensor 408. In some embodiments, the microcontroller 414 can also be configured to communicate remotely with the pilot or another operator that can monitor the pilot's condition. As can be appreciated, the control module 404 can be powered in a number of ways such as internal batteries 416 or another suitable power source. The power source 416 can also be used to power the sensor system 408.

Embodiments of the Sensor System

Figure 5:
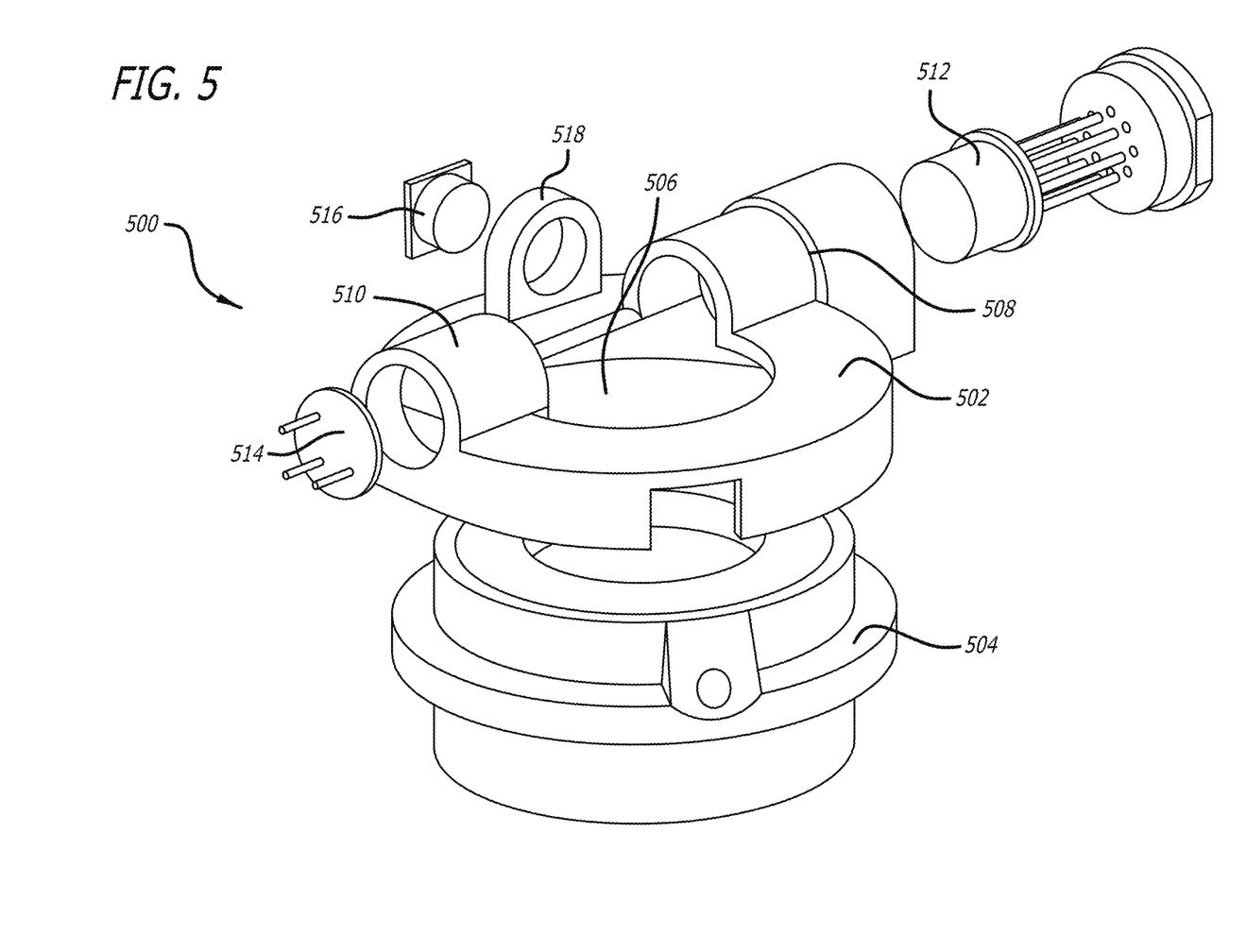
FIG. 5 conceptually illustrates an exploded view of a sensor in accordance with embodiments of the invention.

The sensor system, in accordance with various embodiments can be configured in a number of different ways with any number of different materials and components. One of the key elements of the sensor system is being designed to measure the output of the CO2 from the pilot in real time and while being non-intrusive. FIG. 5 illustrates an embodiment of an in-situ sensor system 500 that is capable of being placed within a mask. For example, many embodiments of a sensor system have a housing portion 502 that is designed to integrate with or fit over an exhale valve 504. In various embodiments, the body 502 has an opening 506 that corresponds to an opening in the exhale valve to allow an unobstructed path for the exhaled air to leave the mask. As can be appreciated, the design of the body can be of any shape such that it engages with the exit valve. Additionally, the housing 502 can have one or more elements that hold the various sensor components. For example, various embodiments can have additional housing elements or mounting elements 508 and 510 that hold the various sensor components. For example, many embodiments of the sensor housing 502 can have mounting elements corresponding to a transmitter end 508 and a receiver end 510. In accordance with many embodiments the transmitter end 508 and the receiver end 510 are aligned such that the signal path between the transmitter end and the receiver end passes over the opening 506 of the housing.

In accordance with many embodiments, the transmitter end 508 can be configured to house and/or hold an optical transmitter element 512 of the sensor. In various embodiments, the optical transmitter element can be a laser or another light source. For example, some embodiments may use fiber coupled lasers that can greatly reduce the complexity of the system without compromising the efficiency. Correspondingly, the receiver end 510 can be configured to house and/or hold an optical receiver element 514. The optical receiver element 514 can be any suitable device that is capable of receiving a signal from the optical transmitter 512. Accordingly, the received signal can be analyzed by a separate control system, as illustrated in FIG. 4 with respect the various levels of CO2 from the pilot.

As previously mentioned, various embodiments may utilize a laser or other form of light source for the optical transmitter element 512. Accordingly, lasers and/or light sources can generate heat which can cause create potential issues for the overall comfort of the pilot as well as the functionality of the system. As such, various embodiments of the sensor system 500 can be configured with a temperature-reading thermistor 516 While the thermistor 516 is positioned in a flange element 518 that forms a portion of the housing 502, it can be appreciated that other embodiments may have one or more thermistors 516 within the sensor system 500. Some embodiments may be embedded in other portions of the housing. In various embodiments, the thermistor can measure the temperature output from an optical transmitter and be connected to a shutoff switch in the control module (not shown). If the temperature of the sensor system gets too high then the switch can cut power to the system to allow it to cool.

Figure 6:
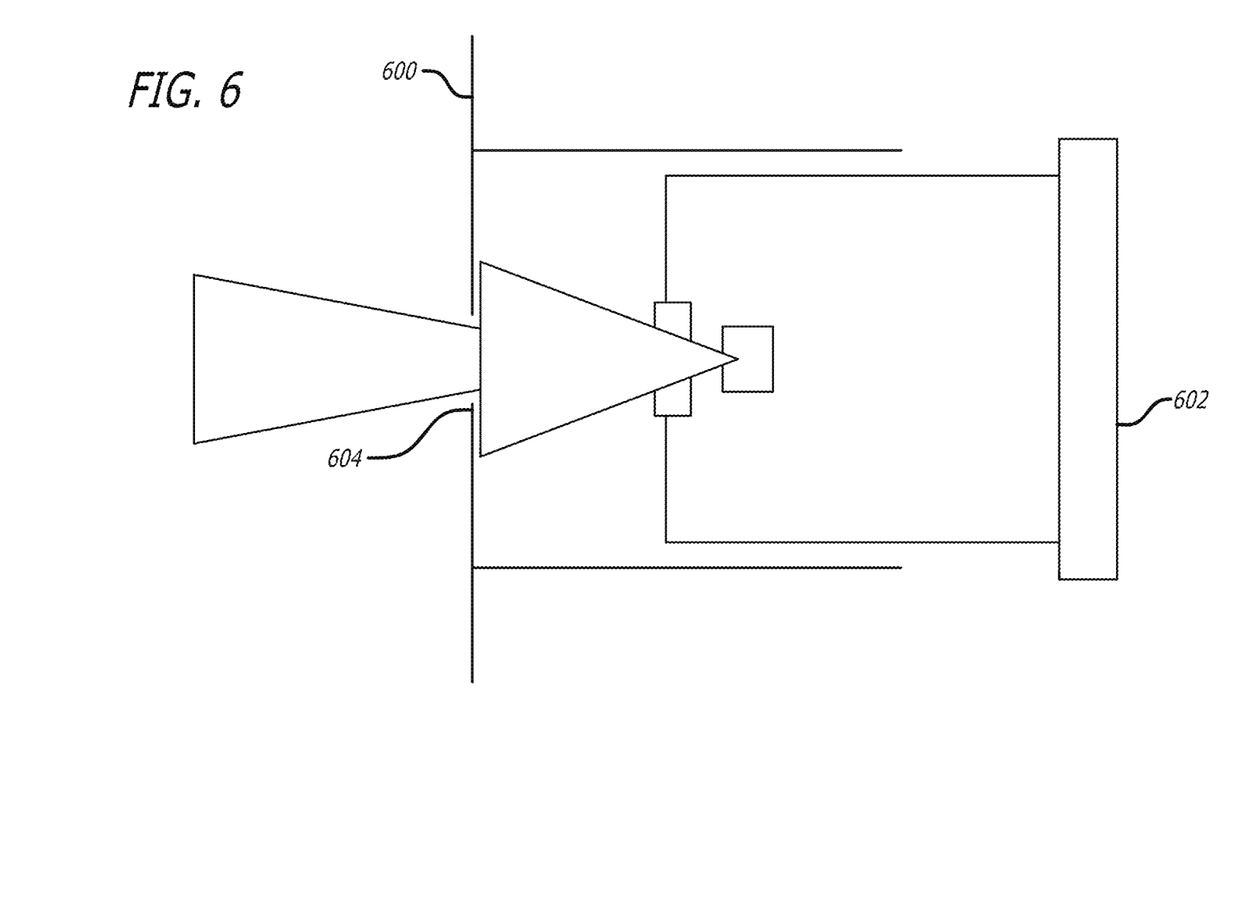
FIG. 6 conceptually illustrates a laser sensor element in accordance with embodiments of the invention.

As previously discussed, the optical transmitter can be any number of devices such as a laser. In some embodiments, the laser can be a Tunable Diode Laser (TDL) that can emit at a wavelength of 2683 nm. The adjustability of the TDL can allow for wavelength ranges that include both CO2 and H2O absorption features. The wavelength of the TDL can be adjusted from the control module previously illustrated. In accordance with various embodiments, the power output from the laser can be controlled or reduced to further help control the heat production while in use. For example, FIG. 6 illustrates a modified housing 600 for a laser 602 that has a small aperture 504 located a short distance from the laser 602. As can be seen the output from the laser 606 is reduced by the aperture 604 producing a smaller output into the mask volume. In some embodiments the laser 602 can have a maximum power output of 9.5 mW that is subsequently reduced by the aperture to less than 500 µW. The aperture 604 can be produced in a number of ways. For example, some embodiments may simply have an aperture disposed in a face of the housing. Other embodiments may utilize a housing with a step-down profile such that the opening of the housing is gradually reduced to produce the desired output for the system.

As can be readily appreciated, the sensor system described throughout can generate heat that can be potentially harmful to the function and overall use of the system. As such it can be appreciated that the housing elements described in FIGS. 5 and 6 can serve as heat sinks to help dissipate any heat generated by the various sensor components. This can be done with any number of materials and in any number of different configurations so as to maintain the function of the sensor system. Although not shown, some embodiments of the housings can have additional heat sink elements such as fins or appendages that can help to dissipate heat. Furthermore, it can be appreciated that the sensor system will undergo various external forces and pressures during use. As such many embodiments of the sensor system can be manufactured without fasteners. The small fasteners that would be required to secure the various components can pose potential inhalation hazards for the pilot if they were to become loose within the volume of the mask. As such, many embodiments can use heat stable adhesives to bond the various sensor components to the housing as well as the housing to the exhale valve.

Figure 7A:
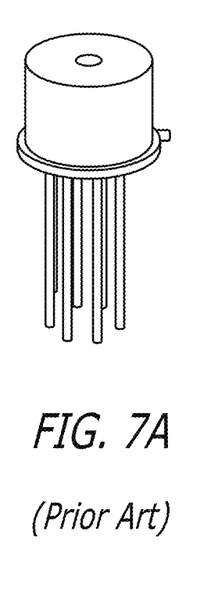
FIGS. 7A and 7B illustrate various laser elements with known art.
Figure 7B:
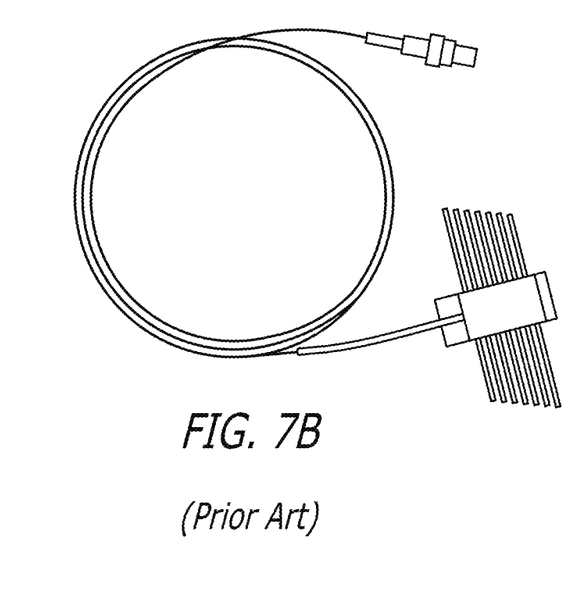

The Laser element and housing described in relation to FIGS. 5 and 6 illustrates an embodiment of a free space laser element that can be used within an in-situ mask sensor system. FIG. 7A illustrates a traditional free space laser that some embodiments can utilize for the sensor system. Free space lasers as illustrated in FIG. 7A represent a laser packaging solution that can require the laser package to be placed in close proximity to the region that is being probed making miniaturization and thermal control difficult often resulting use of more complex cooling elements and requiring more complex maintenance procedures. Some embodiments of sensor systems described herein can be configured to utilize a fiber coupled laser system as shown in FIG. 7B. While relatively known in the art, fiber coupled lasers can be used to simplify the size and complexity of an in-situ mask sensor system. Accordingly, some embodiments of the sensor system may utilize a fiber coupled laser element.

Doctrine of Equivalents

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims

What is claimed is:

1. An in-situ sensor system comprising
a main housing, wherein the main housing is configured to cooperatively engage with an exhalation valve of an oxygen mask configured with a voluminous breathing chamber and wherein the main housing has an opening disposed therein that corresponds with an opening in the exhalation valve of the mask, and is disposed within the voluminous breathing chamber,
an optical transmitter housing disposed on the main housing and configured to house an optical transmitter element,
an optical receiver housing disposed on the main housing and configured to house an optical receiver element, and
wherein the optical transmitter element is optically aligned with the optical receiver element such that a signal path between the optical transmitter element and the optical receiver element transects the opening in the main housing such that exhaled air from a user of the mask will pass through the signal path as it is pushed through the exhalation valve.

2. The in-situ sensor system of claim 1, wherein the optical transmitter element is a laser.

3. The in-situ sensor system of claim 2, wherein the laser is a tunable laser.

4. The in-situ sensor system of claim 3, wherein the laser is tunable to a wavelength suitable for detecting $CO_2$.

5. The in-situ sensor system of claim 3, wherein the laser is tunable to a wavelength suitable for detecting $H_2O$.

6. The in-situ sensor system of claim 1, wherein the optical transmitter housing has a power reducing aperture disposed in a front face of the housing such that the power reducing aperture effectively reduces the power output of the optical transmitter into the volume of the mask by blocking a portion of the signal path limiting.

7. The in-situ sensor system of claim 1, wherein the optical transmitter housing has a step-down profile producing a smaller opening at an exit end of the housing that effectively reduces the power output from the optical transmitter.

8. The in-situ sensor system of claim 6, wherein the laser has a maximum power output of 9.5 mW and the power reducing aperture reduces the power to less than 500 µW.

9. The in-situ sensor system of claim 7, wherein the laser has a maximum power output of 9.5 mW and the smaller opening reduces the power output to less than 500 µW.

10. The in-situ sensor system of claim 1, further comprising a temperature sensor disposed on the main housing and configured to measure the temperature of the sensor system.

11. The in-situ sensor system of claim 1, further comprising a plurality of electrical connections between the optical transmitter and the optical receiver, and an external control module, wherein the control module is configured to receive and analyze data from the sensor system.

12. The in-situ sensor system of claim 11, wherein the control module is configured to analyze the relative content of $CO_2$ and/or $H_2O$ in the exhaled air and wherein the control module further comprises one or more feedback elements to provide feedback to the user with respect to the relative content of $CO_2$ and $H_2O$.

13. The in-situ sensor system of claim 11, wherein the plurality of electrical connections are configured to be disconnectable from the mask through a connection port disposed on an exterior surface of the mask.

14. The in-situ sensor system of claim 1, wherein the optical transmitter and the optical receiver are a fiber coupled laser.

15. A pilot oxygen mask system comprising:
an in-situ sensor system, wherein the in-situ sensor system comprises, a main housing, wherein the main housing is configured to cooperatively engage with an exhalation valve of an oxygen mask configured with a voluminous breathing chamber and wherein the main housing has an opening disposed therein that corresponds with an opening in the exhalation valve of the mask, and is disposed within the voluminous breathing chamber, an optical transmitter housing disposed on the main housing and configured to house an optical transmitter element, an optical receiver housing disposed on the main housing and configured to house an optical receiver element, and wherein the optical transmitter element is optically aligned with the optical receiver element such that a signal path between the optical transmitter element and the optical receiver element transects the opening in the main housing such that exhaled air from a user of the mask will pass through the signal path as it is pushed through the exhalation valve.

\* \* \* \* \*